(12) United States Patent
Kendrick

(10) Patent No.: US 9,549,749 B2
(45) Date of Patent: Jan. 24, 2017

(54) SURGICAL FORCEPS

(71) Applicant: COVIDIEN LP, Mansfield, MA (US)

(72) Inventor: Stephen M. Kendrick, Broomfield, CO (US)

(73) Assignee: COVIDIEN LP, Mansfield, MA (US)

( * ) Notice: Subject to any disclaimer, the term of this patent is extended or adjusted under 35 U.S.C. 154(b) by 582 days.

(21) Appl. No.: 14/032,486

(22) Filed: Sep. 20, 2013

(65) Prior Publication Data

US 2014/0100600 A1 Apr. 10, 2014

Related U.S. Application Data

(60) Provisional application No. 61/711,079, filed on Oct. 8, 2012.

(51) Int. Cl.
*A61B 17/00* (2006.01)
*A61B 17/28* (2006.01)
*A61B 17/29* (2006.01)
*A61B 17/32* (2006.01)
(Continued)

(52) U.S. Cl.
CPC .............. *A61B 17/282* (2013.01); *A61B 17/29* (2013.01); *A61B 17/320092* (2013.01); *A61B 18/18* (2013.01); *A61B 2017/2926* (2013.01); *A61B 2017/2933* (2013.01); *A61B 2017/2936* (2013.01); *A61B 2017/2944* (2013.01);
(Continued)

(58) Field of Classification Search
CPC ............... A61B 2017/2909; A61B 2017/2932; A61B 2017/2933; A61B 2017/2938; A61B 2017/2936; A61B 2017/2944; B25B 13/18; B25B 13/58; B25B 5/163; B25B 5/166; B25B 7/02; B25B 7/04

USPC .......... 81/352, 353, 354, 355; 606/205, 206, 606/207, 208
See application file for complete search history.

(56) References Cited

U.S. PATENT DOCUMENTS 1,517,302 A 12/1924 McNerney
D249,549 S 9/1978 Pike
D263,020 S 2/1982 Rau, III
(Continued)

FOREIGN PATENT DOCUMENTS

CN 201299462 9/2009
DE 2415263 A1 10/1975
(Continued)

OTHER PUBLICATIONS

U.S. Appl. No. 08/926,869, filed Sep. 10, 1997, James G. Chandler.
(Continued)

*Primary Examiner* — Tuan V Nguyen

(57) ABSTRACT

A forceps includes an end effector assembly having first and second jaw members disposed in parallel orientation relative to one another. One or both of the jaw members is movable along a first axis relative to the other jaw member between a spaced-apart position and an approximated position for grasping tissue therebetween. The first and second jaw members are configured to maintain the parallel orientation therebetween upon movement of the jaw members between the spaced-apart and approximated positions. A drive bar is coupled to one or both of the jaw members. The drive bar is selectively movable along a second axis that is different from the first axis between first and second positions for moving the jaw members between the spaced-apart and approximated positions.

8 Claims, 10 Drawing Sheets

(51) Int. Cl.
*A61B 18/18* (2006.01)
*A61B 18/00* (2006.01)

(52) U.S. Cl.
CPC ............. *A61B 2018/0063* (2013.01); *A61B 2018/00196* (2013.01)

(56) References Cited

U.S. PATENT DOCUMENTS

| | | |
|---|---|---|
| 4,711,240 A | 12/1987 | Goldwasser et al. |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| 5,403,312 A | 4/1995 | Yates et al. |
| D358,887 S | 5/1995 | Feinberg |
| 5,507,773 A | 4/1996 | Huitema et al. |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| 6,361,534 B1 | 3/2002 | Chen et al. |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| 6,582,451 B1 * | 6/2003 | Marucci ................ A61B 17/29 606/207 |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,566,334 B2 | 7/2009 | Christian et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| 8,292,888 B2 | 10/2012 | Whitman |
| 8,317,787 B2 | 11/2012 | Hanna |
| 2003/0114851 A1 | 6/2003 | Truckai et al. |
| 2004/0267304 A1 | 12/2004 | Zannis et al. |
| 2005/0165429 A1 | 7/2005 | Douglas et al. |
| 2006/0264922 A1 | 11/2006 | Sartor et al. |
| 2007/0267304 A1 * | 11/2007 | Portier ................ B65D 51/185 206/204 |
| 2012/0283734 A1 | 11/2012 | Ourada |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 4412171 A1 | 10/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 0503662 A1 | 9/1992 |
| EP | 1281878 A1 | 2/2003 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |

(56) References Cited

FOREIGN PATENT DOCUMENTS

| JP | 2004-517668 A | 6/2004 |
|---|---|---|
| JP | 2004-528869 A | 9/2004 |
| JP | 2005-152663 A | 6/2005 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02045589 A3 | 9/2002 |
| WO | 2006/021269 A1 | 3/2006 |
| WO | 2005110264 A3 | 4/2006 |
| WO | 2008/005411 A2 | 1/2008 |
| WO | 2008/040483 A1 | 4/2008 |
| WO | 2008/118728 A1 | 10/2008 |
| WO | 2011/018154 A1 | 2/2011 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,775, filed May 14, 2012, James D. Allen, IV.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/708,335, filed Dec. 7, 2012, Dumbauld.
U.S. Appl. No. 13/731,674, filed Dec. 31, 2012, Siebrecht.
U.S. Appl. No. 13/799,173, filed Mar. 13, 2013, Larson.
U.S. Appl. No. 13/803,636, filed Mar. 14, 2013, Kerr.
U.S. Appl. No. 13/803,762, filed Mar. 14, 2013, Kerr.
U.S. Appl. No. 13/803,884, filed Mar. 14, 2013, Kerr.
U.S. Appl. No. 13/804,010, filed Mar. 14, 2013, Kerr.
U.S. Appl. No. 13/833,823, filed Mar. 15, 2013, Garrison.
U.S. Appl. No. 13/834,703, filed Mar. 15, 2013, Garrison.
U.S. Appl. No. 13/835,004, filed Mar. 15, 2013, Twomey.
U.S. Appl. No. 13/838,945, filed Mar. 15, 2013, Stoddard.
U.S. Appl. No. 13/868,732, filed Apr. 23, 2013, Mueller.
U.S. Appl. No. 13/893,527, filed May 14, 2013, Horner.
U.S. Appl. No. 13/903,091, filed May 28, 2013, Nau.
U.S. Appl. No. 13/903,116, filed May 28, 2013, Nau.
U.S. Appl. No. 13/903,223, filed May 28, 2013, Payne.
U.S. Appl. No. 13/909,362, filed Jun. 4, 2013, Kerr.
U.S. Appl. No. 13/911,674, filed Jun. 6, 2013, Kerr.
U.S. Appl. No. 13/920,643, filed Jun. 18, 2013, Nau.
U.S. Appl. No. 13/922,377, filed Jun. 20, 2013, Allen.
U.S. Appl. No. 13/922,975, filed Jun. 20, 2013, McKenna.
U.S. Appl. No. 13/933,409, filed Jul. 2, 2013, Mueller.
U.S. Appl. No. 13/933,683, filed Jul. 2, 2013, Nau.
U.S. Appl. No. 13/936,510, filed Jul. 8, 2013, Kerr.
U.S. Appl. No. 13/947,991, filed Jul. 22, 2013, Kerr.
U.S. Appl. No. 13/969,204, filed Aug. 16, 2013, Bucciaglia.
U.S. Appl. No. 13/969,278, filed Aug. 16, 2013, Kerr.
U.S. Appl. No. 14/017,572, filed Sep. 4, 2013, Arya.
U.S. Appl. No. 14/019,031, filed Sep. 5, 2013, Garrison.
U.S. Appl. No. 14/019,094, filed Sep. 5, 2013, Garrison.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.

(56) References Cited

OTHER PUBLICATIONS

Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
European Search Report EP 13 18 7674 dated Jan. 30, 2014.

\* cited by examiner

SURGICAL FORCEPS

CROSS REFERENCE TO RELATED APPLICATION

The present application claims the benefit of and priority to U.S. Provisional Application Ser. No. 61/711,079, filed on Oct. 8, 2012, the entire contents of which are incorporated herein by reference.

BACKGROUND

Technical Field

The present disclosure relates to surgical instruments and, more particularly, to surgical forceps for grasping, treating, and/or dividing tissue.

Background of Related Art

A surgical forceps is a plier-like instrument which relies on mechanical action between its jaw members to grasp, clamp, and constrict tissue. Energy-based surgical forceps utilize both mechanical clamping action and energy, e.g., RF energy, ultrasonic energy, microwave energy, thermal energy, light energy, etc., to affect hemostasis by heating tissue and blood vessels to coagulate and/or cauterize tissue. Certain surgical procedures require more than simply coagulating/cauterizing tissue and rely on the unique combination of clamping pressure, precise energy control, and gap distance (i.e., the distance between opposing jaw members when closed about tissue) to "seal" tissue.

Typically, once tissue is treated, e.g., sealed, the surgeon has to accurately sever the tissue along the newly formed tissue seal. Accordingly, many surgical forceps have been designed which incorporate a knife or blade member that effectively severs the tissue after forming a tissue seal.

SUMMARY

As used herein, the term "distal" refers to that portion that is further from an operator while the term "proximal" refers to that portion that is closer to an operator. As used herein, the term "treat" refers to performing a surgical treatment to tissue using energy. The term "energy" refers broadly to include all types of energy used to treat tissue, e.g., RF energy, ultrasonic energy, microwave energy, thermal energy, light energy, etc. Further, any or all of the aspects described herein, to the extent they are consistent, may be used in conjunction with any of the other aspects described herein.

In accordance with aspects of the present disclosure, a forceps is provided including an end effector assembly having first and second jaw members disposed in parallel orientation relative to one another. One (or both) of the jaw member is movable along a first axis relative to the other jaw member between a spaced-apart position and an approximated position for grasping tissue therebetween. The first and second jaw members are configured to maintain the parallel orientation therebetween upon movement of the jaw members between the spaced-apart and approximated positions. A drive bar is coupled to one or both of the jaw members. The drive bar is selectively movable along a second axis that is different from the first axis between first and second positions for moving the jaw members between the spaced-apart and approximated positions.

In one aspect, the first and second axes are perpendicular to one another such that the jaw members are movable in a perpendicular direction relative to the drive bar.

In another aspect, the first and second jaw members are coupled to an outer shaft. In such an aspect, the drive bar is selectively movable along the second axis relative to the outer shaft.

In another aspect, the drive bar defines at least one cam slot having a first portion and a second portion. The first portion of the cam slot defines a longitudinal configuration and the second portion of the cam slot extends in a generally diagonal direction relative to the first portion. The first portion of the cam slot is configured to slidably receive a pin of the outer shaft and the second portion of the cam slot is configured to slidably receive a pin of one (or each) of the jaw members such that translation of the drive bar along the second axis effects movement of one or both jaw members along the first axis.

In still another aspect, one or both of the jaw members is configured for slidable inter-fit engagement with the outer shaft to restrict movement of the jaw members to along the first axis, thereby maintaining the parallel orientation between the jaw members upon movement of the jaw members between the spaced-apart and approximated positions.

In yet another aspect, the outer shaft and one (or both) of the jaw members each include a T-shaped flange. The T-shaped flanges are configured for slidable inter-fit engagement with one another.

In still yet another aspect, the first and second jaw members are configured for slidable inter-fit engagement with one another to restrict movement of the jaw members to along the first axis, thereby maintaining the parallel orientation between the jaw members upon movement of the jaw members between the spaced-apart and approximated positions.

In another aspect, one of the jaw members includes an alignment pillar and the other jaw member includes an alignment slot. The alignment pillars and alignment slots are configured for slidable inter-fit engagement with one another to inhibit relative movement of the jaw members off of the first axis.

In yet another aspect, one (or both) of the jaw members are configured for slidable inter-fit engagement with the drive bar to restrict movement of the jaw members to along the first axis, thereby maintaining the parallel orientation between the jaw members upon movement of the jaw members between the spaced-apart and approximated positions.

In another aspect, the first and second jaw members are slidable diagonally along the first axis and the drive bar is selectively translatable longitudinally along the second axis.

Another forceps provided in accordance with aspects of the present disclosure includes an end effector assembly having first and second jaw members. The first and second jaw members are disposed in parallel orientation relative to one another. One (or both) of the jaw members is movable relative to the other along a first axis between a spaced-apart position and an approximated position for grasping tissue therebetween. The first and second jaw members are disposed in slidable inter-fit engagement with one another to maintain the parallel orientation between the jaw members upon movement of the jaw members between the spaced-apart and approximated positions.

In one aspect, one (or both) of the jaw members includes an alignment pillar. The other jaw member includes an alignment slot defined therein. The alignment pillar and alignment slot are configured for slidable inter-fit engagement with one another to inhibit relative movement of the jaw members off of the first axis.

In another aspect, the alignment pillar and the alignment slot define complementary keying features.

In still another aspect, a drive bar is provided. The drive bar is coupled to one (or both) of the jaw members and is selectively movable along a second axis different from the first axis for moving the jaw members between the spaced-apart and approximated positions.

In yet another aspect, the first and second axes are perpendicular to one another such that the jaw members are movable in a perpendicular direction relative to the drive bar.

Provided in accordance with other aspects of the present disclosure is another forceps including an end effector assembly having first and second jaw members. The first and second jaw members are disposed in parallel orientation relative to one another. One (or both) of the jaw members is movable along a first axis relative to the other jaw member between a spaced-apart position and an approximated position for grasping tissue therebetween. A drive bar is coupled to one (or both) of the jaw members. The drive bar is selectively movable along a second axis different from the first axis between first and second positions for moving the jaw members between the spaced-apart and approximated positions. The drive bar and one (or both) of the jaw members are disposed in inter-fit engagement with one another to maintain the parallel orientation between the jaw members upon movement of the jaw members between the spaced-apart and approximated positions.

In one aspect, the drive bar includes a distal engagement portion including one or more cut-outs. In such an aspect, one (or both) of the jaw members includes a proximal flange portion. The proximal flange portion(s) of the jaw member(s) is configured for slidable inter-fit engagement with the cut-out(s) of the distal engagement portion of the drive bar to maintain the parallel orientation between the jaw members upon movement of the jaw members between the spaced-apart and approximated positions.

In another aspect, the proximal flange portion(s) of the jaw member(s) is slidable relative to the cut-out(s) of the distal engagement portion of the drive bar along the first axis. Alternatively, the proximal flange portion(s) of the jaw member(s) may be slidable relative to the cut-out(s) of the distal engagement portion of the drive bar along a third axis that is diagonal to both the first and second axes.

In still another aspect, the first and second jaw members are coupled to an outer shaft. The drive bar, in such an aspect, is selectively movable relative to the outer shaft along the second axis.

In another aspect, the outer shaft defines one or more cam slots configured to slidably receive a pin of one (or both) of the jaw members. According to this configuration, translation of the drive bar along the second axis effects movement of the jaw members relative to one another along the first axis.

BRIEF DESCRIPTION OF THE DRAWINGS

Various aspects of the present disclosure are described herein with reference to the drawings wherein like reference numerals identify similar or identical elements.

DETAILED DESCRIPTION

Figure 1:
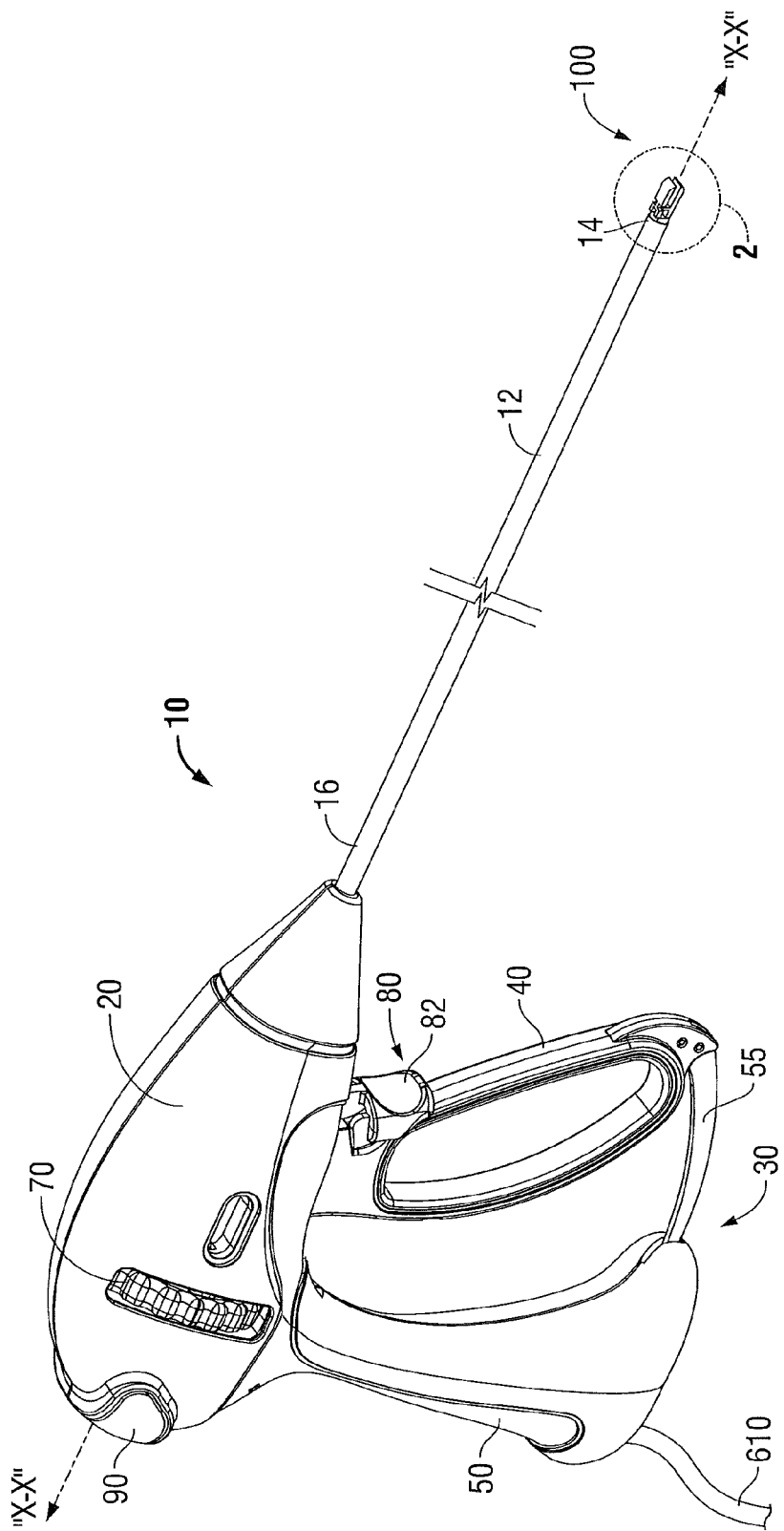
FIG. 1 is a perspective view of an endoscopic surgical forceps configured for use in accordance with the present disclosure.
Figure 2:
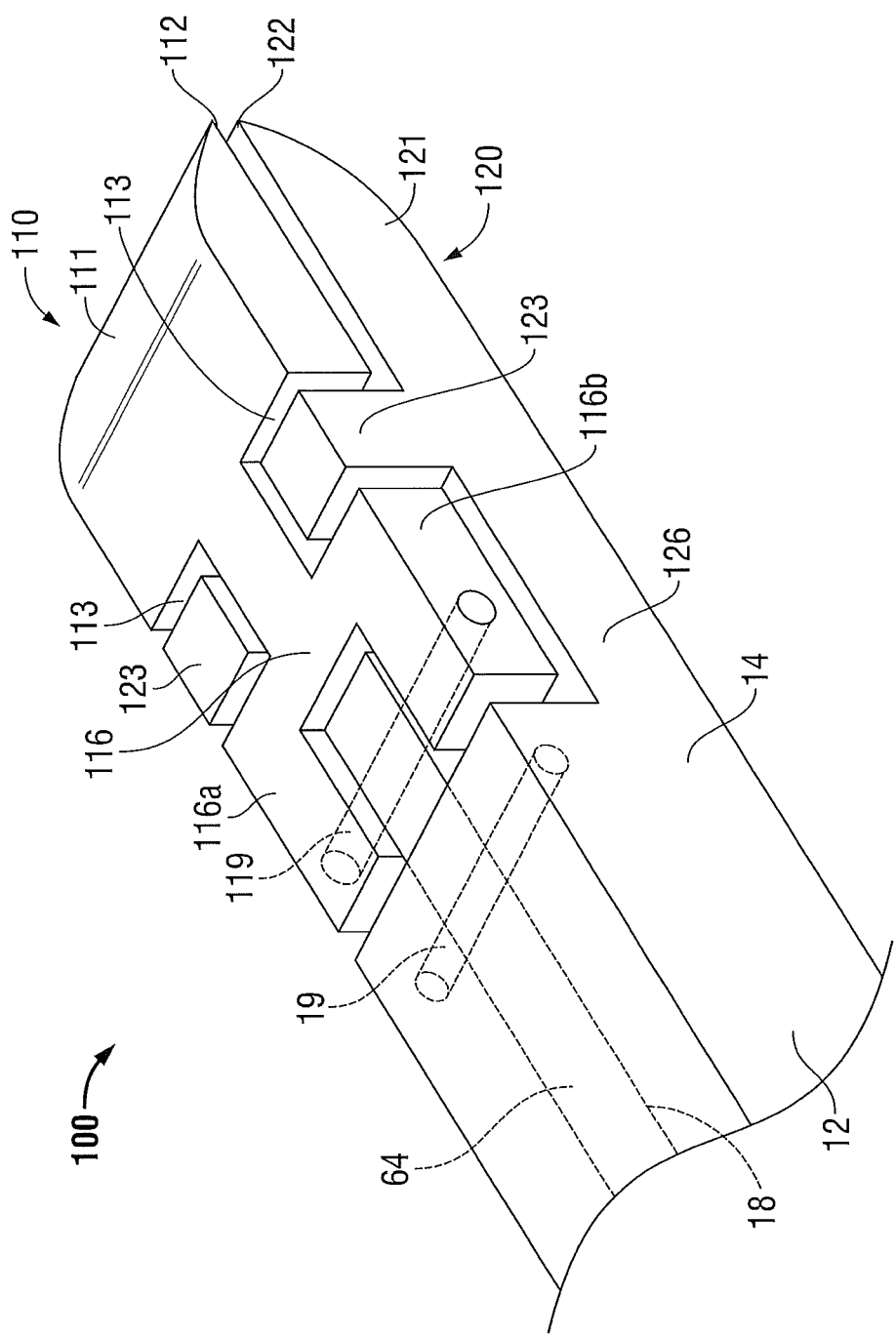
FIG. 2 is an enlarged, perspective view of a distal end of the forceps of FIG. 1 including an end effector assembly coupled thereto and configured for use therewith.
Figure 3:
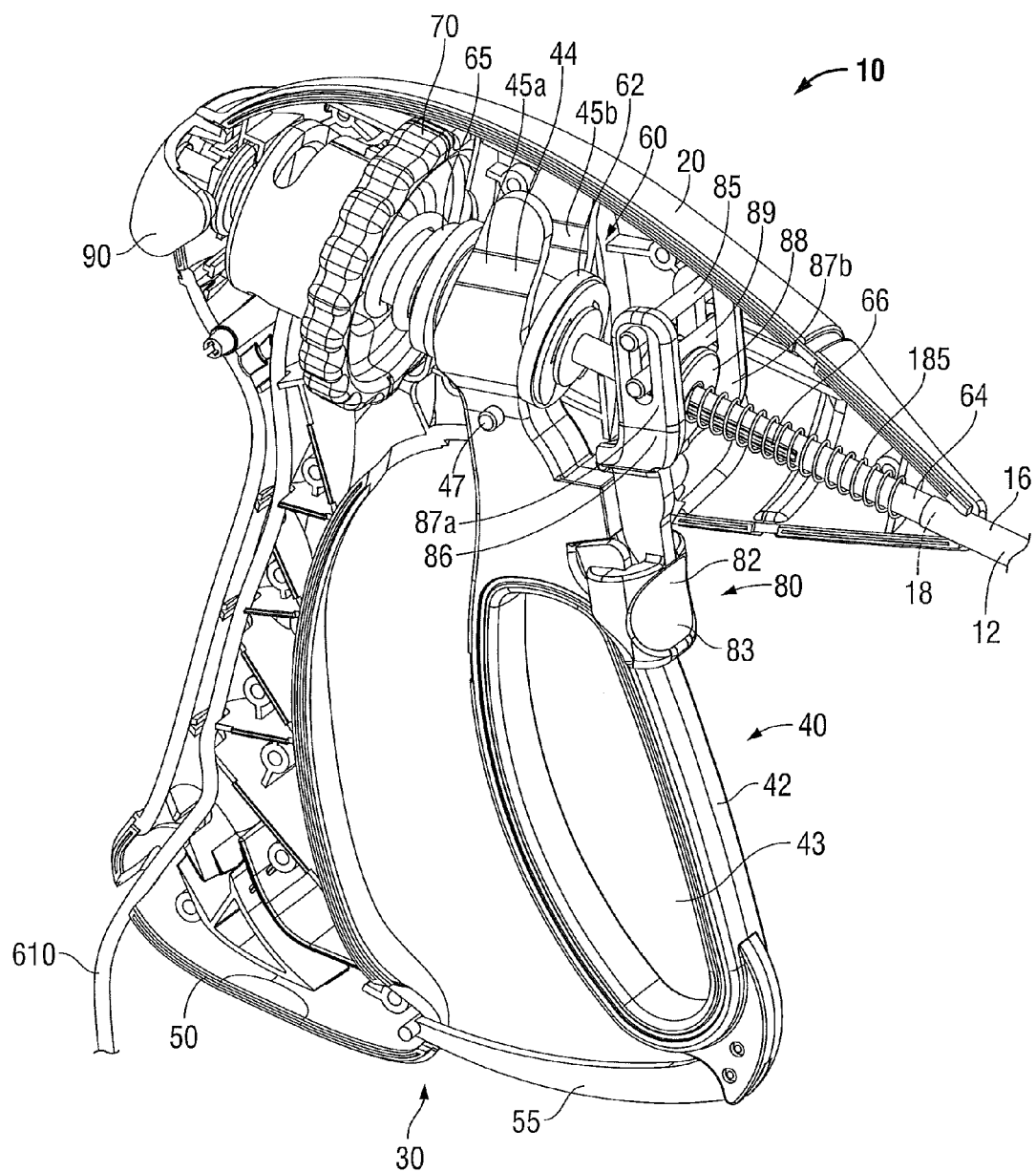
FIG. 3 is an enlarged, perspective view of a proximal end of the forceps of FIG. 1 wherein a portion of the housing has been removed to show the internal components thereof.
Figure 4:
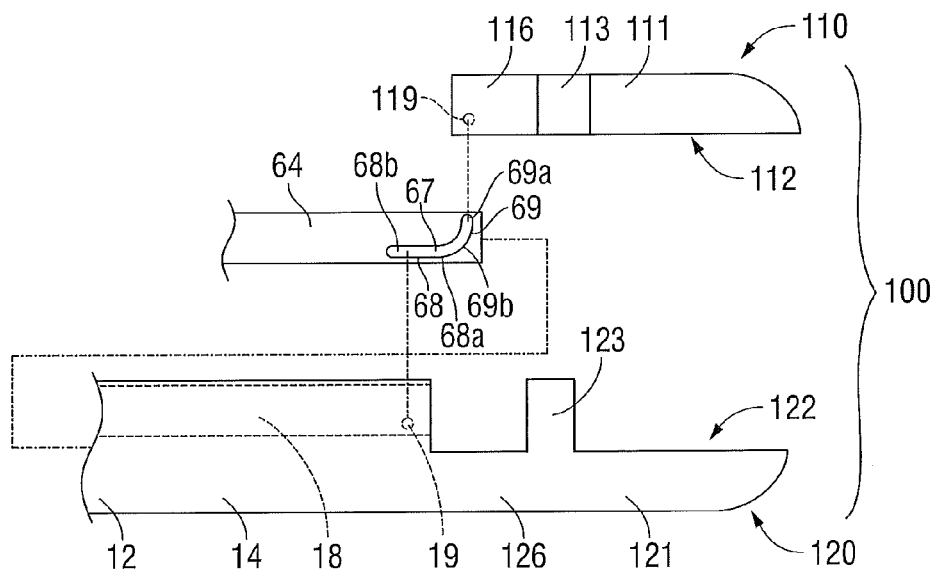
FIG. 4 is a side view of the end effector assembly of FIG. 2 shown with parts separated.

Referring to FIGS. 1-3, an endoscopic surgical forceps provided in accordance with the present disclosure is shown generally identified by reference numeral 10. Although shown configured for use in endoscopic surgical procedures, forceps 10 may alternatively be configured for use in connection with traditional open surgical procedures. That is, for the purposes herein, either an endoscopic instrument, e.g., forceps 10, or an open instrument may be utilized in accordance with the present disclosure. Obviously, different connections and considerations apply to each particular type of instrument; however, the novel aspects with respect to the end effector assembly and its operating characteristics remain generally consistent with respect to both the open and endoscopic configurations.

With continued reference to FIGS. 1-3, forceps 10 defines a longitudinal axis "X-X" and generally includes a housing 20, a handle assembly 30, a rotating assembly 70, a trigger assembly 80, and an end effector assembly 100. Forceps 10 further includes a shaft 12 having a distal end 14 configured to engage end effector assembly 100 and a proximal end 16 that engages housing 20. Forceps 10 also includes a cable 610 that connects forceps 10 to a generator (not shown) or other suitable power source, although forceps 10 may alternatively be configured as a handheld instrument having a portable battery (not shown) and generator (not shown) disposed within housing 20.

Handle assembly 30 includes a fixed handle 50 and a movable handle 40. Fixed handle 50 is integrally associated with housing 20 and movable handle 40 is movable relative to fixed handle 50, as will be explained in greater detail below, to impart movement of jaw members 110, 120 of end effector assembly 100 between a spaced-apart position (FIG. 5A) and an approximated position (FIG. 5B) to grasp tissue therebetween. Rotating assembly 70 is operatively associated with housing 20 and is rotatable about longitudinal axis "X-X" to rotate end effector assembly 100 about longitudinal axis "X-X." Trigger assembly 80, as will be described in greater detail below, is selectively actuatable to deploy a knife 184 (FIGS. 16-17B) between jaw members 110, 120 to cut tissue grasped therebetween.

Referring still to FIGS. 1-3, end effector assembly 100 is coupled to a distal end 14 of shaft 12 and includes a pair of jaw members 110, 120. End effector assembly 100 is designed as a unilateral assembly, i.e., where jaw member 120 is fixed relative to shaft 12 and jaw member 110 is movable relative to shaft 12 and fixed jaw member 120. However, end effector assembly 100 may alternatively be configured as a bilateral assembly, i.e., where both jaw members 110, 120 are movable relative to one another and to shaft 12.

Each of the jaw members 110, 120 of end effector assembly 100 defines a respective tissue-treating surface 112, 122 (FIG. 2), which may be in the form of a conductive plate disposed atop an otherwise insulative jaw member. Either or both of tissue-treating surfaces 112, 122 are adapted to connect to a source of energy, e.g., a generator (not shown), to transmit energy between tissue-treating surfaces 112, 122 and through tissue grasped between jaw members 110, 120 to treat, e.g., seal, tissue. More specifically, a wire (or wires) (not shown) may extend from cable 610 (FIG. 1), through housing 20 and shaft 12, ultimately connecting to one or both of tissue-treating surfaces 112, 122 for supplying energy thereto, although other configurations are also contemplated. Either or both tissue-treating surfaces 112, 122 of jaw members 110, 120, respectively, may further define a longitudinally-oriented knife channel 115, 125, respectively, that is configured to facilitate and guide the extension of knife 184 (FIGS. 16-17B) between jaw members 110, 120 to cut tissue grasped therebetween, as will be described in greater detail below.

Referring to FIG. 2, end effector assembly 100 is configured to facilitate parallel closure of jaw members 110, 120 about tissue and, thus, to help promote effective and uniform treatment of tissue. With respect to tissue sealing in particular, clamping pressure, e.g., the pressure applied by the jaw members to tissue grasped therebetween, and gap distance, e.g., the distance between the jaw members when grasping tissue therebetween, are factors in achieving an effective tissue seal. Typically, the desired closure pressure is within the range of about 3 kg/cm$^2$ to about 16 kg/cm$^2$, while the desired gap distance is within the range of about 0.001 inches to about 0.006 inches. Parallel jaw closure facilitates the formation of an effective tissue seal across the entire area of tissue to be sealed by maintaining a uniform gap distance between the jaw members and a uniform closure pressure applied to tissue. The specific features and configuration of end effector assembly 100 that promote parallel jaw closure will be described in greater detail below. Various other embodiments of end effector assemblies similar to end effector assembly 100 and also configured for parallel jaw closure will likewise be described in detail in turn below.

With reference again to FIG. 1, in conjunction with FIG. 2, movable handle 40 of handle assembly 30 is ultimately connected to a drive assembly 60 (FIG. 3) that, together, mechanically cooperate to impart movement of jaw members 110 and 120 between a spaced-apart position and an approximated position to grasp tissue between tissue-treating surfaces 112, 122 of jaw members 110, 120, respectively. A ratchet assembly 55 may also be included for selectively locking jaw members 110, 120 relative to one another at various positions during pivoting, e.g., for selectively locking jaw members 110, 120 in one or more approximated positions.

As best shown in FIG. 3, movable handle 40 defines a grasping portion 42 including a finger hole 43 to facilitate grasping and manipulation by the user, and a bifurcated upper portion 44 that extends upwardly into housing 20. Bifurcated upper portion 44 includes first and second flanges 45a, 45b that extend about and are engaged to a mandrel 62 of drive assembly 60 on either side thereof. Flanges 45a, 45b are pivotably coupled to housing 20 via a pivot pin 47 that is disposed below drive bar 64 of drive assembly 60. Mandrel 62, in turn, is engaged about drive bar 64 such that, upon pivoting of movable handle 40 from an initial position, wherein movable handle 40 is spaced-apart from fixed handle 50, to a compressed position, wherein movable handle 40 is disposed in close proximity to fixed handle 50, drive bar 64 is urged distally through shaft 12 and relative to end effector assembly 100 (FIG. 2) to move jaw members 110, 120 (FIG. 2) from the spaced-apart position to the approximated position to grasp tissue therebetween. Alternatively, pivot pin 47 may be positioned above drive bar 64 such that drive bar 64 is pulled proximally through shaft 12 and relative to end effector assembly 100 (FIG. 2) upon pivoting of movable handle 40 from the initial position to the actuated position. In such a configuration, drive bar 64 and end effector assembly 100 (FIG. 2) are configured such that proximal translation of drive bar 64 relative to end effector assembly 100 (FIG. 2) effects movement of jaw members 110, 120 (FIG. 2) from the spaced-apart position to the approximated position to grasp tissue therebetween. A spring 65 engaged between housing 20 and the proximal end of mandrel 62 is provided to bias mandrel 62 proximally, thereby biasing movable handle 40 towards the initial position and jaw members 110, 120 (FIG. 2) towards the spaced-apart position.

Figure 16:
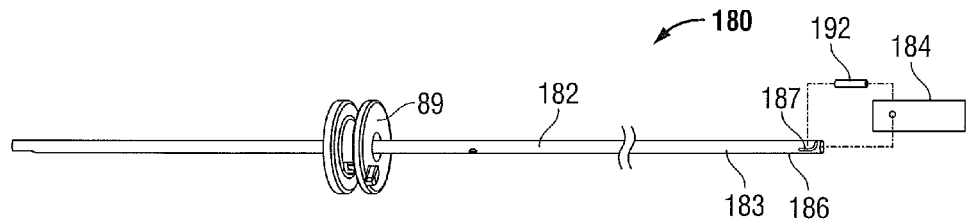
FIG. 16 is a perspective view of a knife assembly configured for use with the forceps of FIG. 1.
Figure 17A:
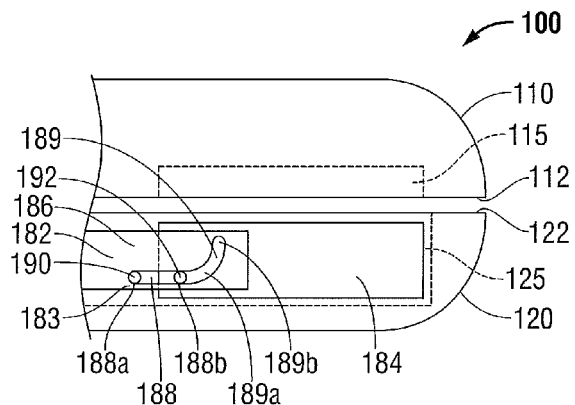
FIG. 17A is a longitudinal, cross-sectional view of the end effector assembly of FIG. 2 shown including a knife disposed in a retracted position.
Figure 17B:
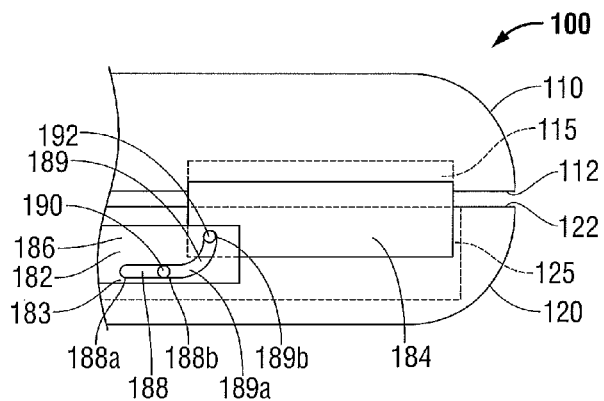
FIG. 17B is a longitudinal, cross-sectional view of the end effector assembly of FIG. 2 shown including the knife disposed in an extended position.

Referring momentarily to FIGS. 16-17B, as mentioned above, forceps 10 may include a knife assembly 180 including a knife bar 182 extending through shaft 12 and a knife 184 coupled to knife bar 182 at the distal end thereof. Knife 184 is initially disposed within the knife channel of one of the jaw members, e.g., knife channel 125 of jaw member 120. As will be described in greater detail below, upon actuation, e.g., upon actuation of trigger 82 of trigger assembly 80, knife bar 182 is translated through shaft 12 and relative to jaw member 120 such that knife 184 is advanced from a retracted position, wherein knife 184 is disposed completely within knife channel 125 of jaw member 120, to an extended position, wherein knife 184 extends from knife channel 125, between jaw members 110, 120, and at least partially into knife channel 115 of jaw member 110 to cut tissue grasped between jaw members 110, 120.

With continued reference to FIGS. 16-17B, and with additional reference to FIGS. 1-3, trigger assembly 80 includes a trigger 82 having a toggle member 83 and a bifurcated arm 86 extending upwardly from toggle member 83 and into housing 20. Arm 86 is bifurcated to define first and second spaced-apart flanges 87a, 87b, respectively, to permit passage of arm 86 about drive assembly 60. Trigger 82 is pivotably coupled to housing 20 via pivot pin 85, which extends through the upper, free ends of flanges 87a, 87b above drive bar 64 of drive assembly 60. A second pin 88 extends between flanges 87a, 87b to couple trigger 82 to ferrule 89. Ferrule 89 is slidably disposed about drive bar 64 and is pinned (or otherwise engaged to) knife bar 182 through a longitudinal slot 66 defined within drive bar 64. Accordingly, upon pivoting of trigger 82 about pivot pin 85 and relative to housing 20 from an un-actuated position to an actuated position, flanges 87a, 87b urge ferrule 89 and, thus, knife bar 182 proximally such that knife 184 is moved from the retracted position (FIG. 17A) to the extended position (FIG. 17B) to cut tissue grasped between jaw members 110, 120. On the other hand, return of trigger 82 towards the un-actuated position rotates flanges 87a, 87b to urge knife bar 182 distally to thereby move knife 184 back to the retracted position within jaw member 120. A spring 185, which is disposed about drive bar 64 and is engaged between ferrule 89 and the distal end of housing 20 biases ferrule 89 distally, thereby biasing trigger 82 towards the un-actuated position and knife 184 towards the retracted position.

Turning now to FIGS. 2 and 4-6, as mentioned above, end effector assembly 100 is configured for use with forceps 10, although end effector assembly 100 may alternatively be configured for use with any other suitable surgical instrument including a longitudinally translatable drive bar for moving jaw members 110, 120 relative to one another between a spaced-apart position and an approximated position for grasping tissue therebetween. End effector assembly 100 is configured to facilitate parallel closure of jaw members 110, 120 about tissue and, thus, to promote effective and uniform treatment of tissue.

Referring additionally to FIG. 3, drive bar 64 of drive assembly 60, as mentioned above, is selectively translatable through shaft 12, e.g., via actuation of movable handle 40, to move jaw members 110, 120 between the spaced-apart position and the approximated position. In particular, drive bar 64 defines a longitudinally-extending cam slot 67 therethrough towards the distal end thereof that is configured to receive first and second pins 19, 119 of end effector assembly 100 such that distal translation of drive bar 64 relative to pins 19, 119 of end effector assembly 100 urges jaw members 110, 120 to move from the spaced-apart position to the approximated position. Cam slot 67 defines a generally longitudinal portion 68 having distal and proximal ends 68a, 68b, respectively, and a curved portion 69 that curves vertically upwardly from the longitudinal portion 68. Curved portion 69 includes a first (upper, distal) end 69a and a second (lower, proximal) end 69b. However, in embodiments where drive assembly 60 is configured to translate drive bar 64 proximally upon actuation of movable handle 40, cam slot 67 is alternatively configured such that the curved portion 69 of cam slot 67 is curved vertically downwardly from the longitudinal portion 68 thereof to achieve the same result, e.g., to move jaw members 110, 120 to the approximated position upon proximal translation of drive bar 64. Further, although a single cam slot 67 including both longitudinal and curved portions 68, 69, respectively, is shown, drive bar 64 may alternatively be configured to include two separate slots: a longitudinal slot and an upwardly curved slot. The curved portion 69 of cam slot 67 (or the curved slot) may also define an angled configuration, rather than a curved configuration.

With continued reference to FIGS. 2 and 4-6, shaft 12 defines a lumen 18 extending longitudinally therethrough that is configured to permit reciprocation of drive bar 64 therethrough. Shaft 12 further includes a first pin 19 fixedly engaged thereto and extending transversely through lumen 18 at the distal end 14 of shaft 12. First pin 19 is configured to be received within longitudinal portion 68 of cam slot 67 defined within drive bar 64 and is longitudinally translatable through cam slot 67 between the distal and proximal ends 68a, 68b, respectively, of longitudinal portion 68 of cam slot 67 to permit translation of drive bar 64 through shaft 12.

One of the jaw members, e.g., jaw member 120, is fixedly engaged to, e.g., monolithically formed with, shaft 12 and extends distally therefrom. Jaw member 120 defines a proximal flange portion 126 that is engaged to shaft 12, and a distal jaw portion 121 that defines the tissue-treating surface 122 of jaw member 120. Distal jaw portion 121 of jaw member 120 further includes a pair of alignment pillars 123 extending from either side thereof in generally perpendicular orientation relative to tissue-treating surface 122. The other jaw member, e.g., jaw member 110, similarly includes a proximal flange portion 116 and a distal jaw portion 111 that defines the tissue-treating surface 112 of jaw member 110. Distal jaw portion 111 of jaw member 110 further includes a pair of alignment slots 113 define therein on each side thereof that extend in generally perpendicular orientation relative to tissue-treating surface 112. Alignment slots 113 are shaped complementary to and are configured to receive alignment pillars 123 of jaw member 120 in inter-fit engagement therewith to maintain the alignment of and parallel orientation between jaw members 110, 120 regardless of the relative position of jaw members 110, 120, e.g., regardless of whether jaw members 110, 120 are disposed in the spaced-apart position, the approximated position, or any position therebetween.

Figure 6:
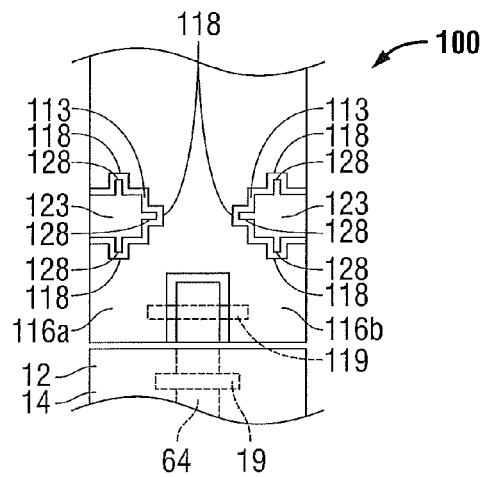
FIG. 6 is a top view of the distal end of the forceps of FIG. 1.

As best shown in FIG. 6, alignment pillars 123 may include a plurality of protrusions 128 extending outwardly therefrom and alignment slots 113 may define a plurality of recesses 118 configured to receive protrusions 128 to further facilitate and maintain the alignment between and parallel orientation of jaw members 110, 120 relative to one another. That is, protrusions 128 and recesses 118 of pillars 123 and slots 113, respectively, establish a "keying" feature between jaw members 110, 120 that helps to ensure alignment and inhibit tilting of jaw members 110, 120 relative to one another. Other "keyed" configurations are also contemplated. Further, the configuration of pillars 123 and alignment slots 113 may be reversed, e.g., wherein the pillars extend from jaw member 110 and the slots are defined within jaw member 120, or each jaw member 110, 120 may include one pillar 123 and one alignment slot 113.

Referring again to FIGS. 2 and 4-6, proximal flange portion 116 of jaw member 110 is bifurcated to define first and second spaced-apart flange components 116a, 116b. Second pin 119 is fixedly engaged to and extends transversely between the spaced-apart flange components 116a, 116b of proximal flange portion 116 of jaw member 110. Second pin 119 is configured to be received within curved portion 69 of cam slot 67 of drive bar 64 and is vertically translatable relative to drive bar 64 as second pin 119 is translated through curved portion 69 of cam slot 67 between the first and second ends 69a, 69b, respectively, thereof, to permit translation of drive bar 64 through and relative to shaft 12.

Figure 5A:
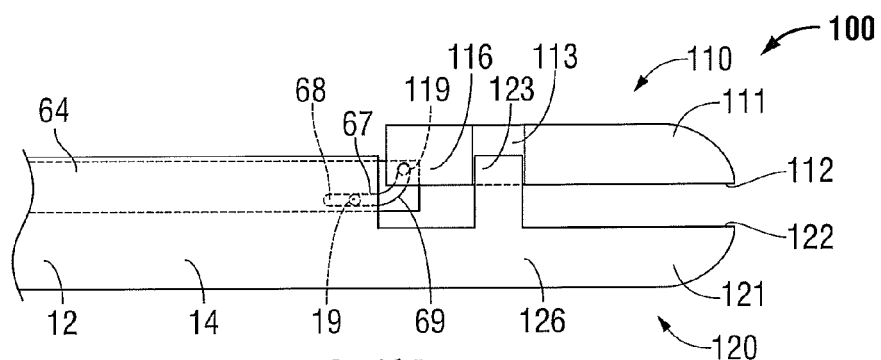
FIG. 5A is a longitudinal, cross-sectional view of the end effector assembly of FIG. 2 wherein jaw members of the end effector assembly are disposed in a spaced-apart position.

The use and operation of forceps 10 and end effector assembly 100 for grasping and treating tissue is described with reference to FIGS. 1-5B. Initially, with jaw members 110, 120 disposed in the spaced-apart position (FIG. 5A), forceps 10 is manipulated and/or maneuvered into position such that tissue to be treated is disposed between tissue-treating surfaces 112, 122 of jaw members 110, 120, respectively. At this point, movable handle 40 is disposed in the initial position and, accordingly, drive bar 64 is disposed in a more-proximal position such that jaw members 110, 120 are disposed in the spaced-apart position. More specifically, in the spaced-apart position, as best shown in FIG. 5A, first pin 19 is disposed at distal end 68a of longitudinal portion 68 of cam slot 67 of drive bar 64, while second pin 119 is disposed at first (upper, distal) end 69a of curved portion 69 of cam slot 67. As such, since first and second pins 19, 119 are vertically-spaced from one-another in this position, jaw members 110, 120 are likewise vertically-spaced from one another, e.g., in the spaced-apart position. Further, in the spaced-apart position, pillars 123 of jaw member 120 are only partially disposed within alignment slots 113 of jaw member 110, but are sufficiently disposed therein so as to maintain the parallel orientation between tissue-treating surfaces 112, 122 of jaw members 110, 120, respectively.

Figure 5B:
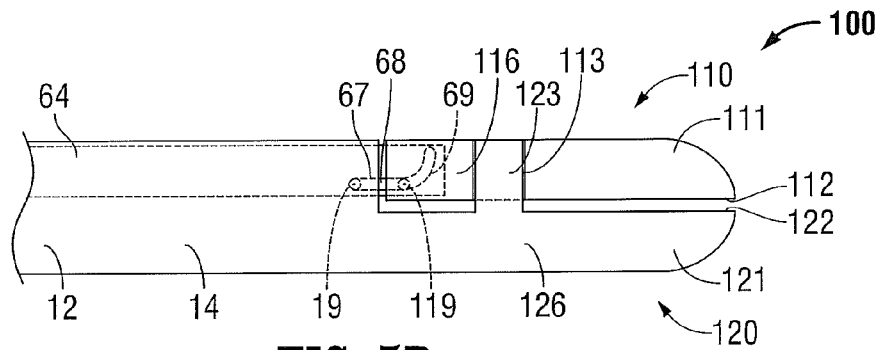
FIG. 5B is a longitudinal, cross-sectional view of the end effector assembly of FIG. 2 wherein the jaw members are disposed in an approximated position.

In order to grasp tissue between tissue-treating surfaces 112, 122 of jaw members 110, 120, respectively, movable handle 40 is compressed, or pulled proximally relative to fixed handle 50 from the initial position to the compressed position to urge drive bar 64 distally. As drive bar 64 is translated distally through lumen 18 of shaft 12 and relative to end effector assembly 100, first pin 19 is moved through longitudinal portion 68 of cam slot 67 from the distal end 68a thereof towards the proximal end 68b thereof, while second pin 119 is moved through curved portion 69 of cam slot 67 from the first (upper, distal) end 69a thereof towards the second (lower, proximal) end 69b thereof. As second pin 119 is urged vertically downwardly due to the vertically-curved configuration of curved portion 69 of cam slot 67 and the distal translation of drive bar 64 relative to second pin 119, jaw member 110 is moved vertically downwardly towards jaw member 120, e.g., towards the approximated position, to grasp tissue therebetween. That is, in the approximated position, as best shown in FIG. 5B, first pin 19 is disposed at proximal end 68b of longitudinal portion 68 of cam slot 67, while second pin 119 is disposed at second (lower, proximal) end 69b of curved portion 69 of cam slot 67 in substantial vertical alignment with first pin 19. As such, with first and second pins 19, 119 vertically-aligned relative to one another, jaw members 110, 120 are disposed in close proximity to one another, e.g., in the approximated position, grasping tissue therebetween.

With jaw members 110, 120 disposed in the approximated position, pillars 123 are substantially disposed within alignment slots 113, with the keyed relationship therebetween maintaining jaw members 110, 120 in parallel orientation relative to one another. More specifically, the keyed engagement between pillars 123 and alignment slots 113 of jaw members 120, 110, respectively, permits movement of jaw member 110 relative to jaw member 120 only in the vertical direction, thereby maintaining the parallel orientation of tissue-treating surfaces 112, 122 of jaw members 110, 120, respectively.

Continuing with reference to FIGS. 1-5B, with jaw members 110, 120 disposed in parallel orientation relative to one another and grasping tissue between tissue-treating surfaces 112, 122, respectively, the gap distance between tissue-treating surfaces 112, 122 of jaw members 110, 120 is uniform along the entire length thereof. Further, the closure pressure applied to tissue (at least where tissue defines a uniform thickness) is also uniform across the entire length of tissue-treating surfaces 112, 122. In this approximated position, tissue-treating surface 112 and/or tissue-treating surface 122 may be energized, e.g., via actuation of activation switch 90 (FIG. 1), to transmit energy between tissue-treating surfaces 112, 122 and through tissue to treat, e.g., seal, tissue. As mentioned above, maintaining a uniform gap distance and closure pressure facilitates effective and uniform tissue treatment, e.g., formation of an effective tissue seal.

At the completion of tissue treatment, or where it is desired to only cut tissue, knife 184 (FIGS. 16-17B) may be moved from the retracted position to the extended position, e.g., via actuation of trigger 82 of trigger assembly 80 (FIG. 1), to cut tissue grasped between jaw members 110, 120. The use, operation, and particular features of knife assembly 180 (FIGS. 16-17B), will be described in detail below. Ultimately, movable handle 40 may be released (or returned) to the initial position, thereby translating drive bar 64 proximally to return jaw members 110, 120 back to the spaced-apart position (FIG. 5A) to release the treated and/or divided tissue.

Figure 7:
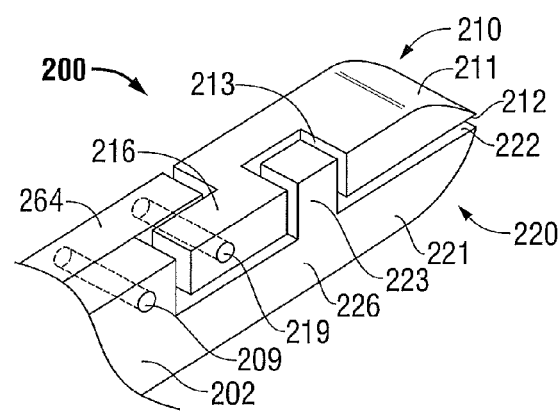
FIG. 7 is a perspective view of another end effector assembly configured for use with the forceps of FIG. 1.

Turning now to FIG. 7, another embodiment of an end effector assembly similar to end effector assembly 100 (FIG. 2) and likewise configured to achieve uniform and parallel jaw closure is shown generally identified by reference numeral 200. End effector assembly 200 differs from end effector assembly 100 (FIG. 2) mainly in that end effector assembly 200 defines an asymmetrical configuration while end effector assembly 100 (FIG. 2) defines a substantially symmetrical configuration. For purposes of brevity, only the differences between end effector assembly 200 and end effector assembly 100 (FIG. 2) will be described in detail below, while similarities will only be summarily described or omitted entirely.

As mentioned above, end effector assembly 200 defines an asymmetrical configuration. More specifically, drive bar 264 extends alongside, e.g., adjacent to, shaft 202, rather than extending through shaft 202 as in the configuration of end effector assembly 100 (FIG. 2). Shaft 202 may define a cut-out portion (not explicitly shown) that is configured to slidably receive drive bar 264 such that the overall dimensions of end effector assembly 200 remain the same regardless of whether drive bar 264 is disposed alongside shaft 202 or extends through a lumen defined within shaft 202.

With continued reference to FIG. 7, similar to end effector assembly 100 (FIG. 2) described above, drive bar 264 is selectively translatable relative to shaft 202 to move jaw members 210, 220 between the spaced-apart and approximated positions. More specifically, drive bar 264 defines a cam slot (similar to cam slot 67 of drive bar 64 (see FIG. 4)) that includes a longitudinal portion and a curved portion extending upwardly and distally from the longitudinal portion. The cam slot (not explicitly shown) is configured to receive first and second pins 209, 219 of end effector assembly 200 such that distal translation of drive bar 264 relative to end effector assembly 200 urges jaw members 210, 220 to move from the spaced-apart position to the approximated position, similarly as described above with respect to end effector assembly 100 (FIG. 2). First pin 209 is fixedly engaged to shaft 202 and extends outwardly therefrom towards drive bar 264, e.g., into the cut-out portion thereof. First pin 209 is received within the cam slot defined within drive bar 264 and is longitudinally translatable through and relative to the longitudinal portion of the cam slot to permit translation of drive bar 264 relative to shaft 202 and jaw members 210, 220.

With continued reference to FIG. 7, one of the jaw members, e.g., jaw member 220, is fixedly engaged to shaft 202 and extends distally therefrom. Jaw member 220 defines an offset proximal flange portion 226 that is fixedly engaged to shaft 202 and a distal jaw portion 221 defining a tissue-treating surface 222 and including an alignment pillar 223 extending from a side thereof in generally perpendicular orientation relative to tissue-treating surface 222. Proximal flange portion 226 is offset relative to a longitudinal axis of jaw member 220 to engage shaft 202 and to provide clearance for translation of drive bar 264 along and relative to shaft 202 and proximal flange portion 226 of jaw member 220. Pillar 223 is similarly offset from the longitudinal axis of jaw member 220, although other configurations are contemplated.

The other jaw member, e.g., jaw member 210, likewise includes a proximal flange portion 216, and a distal jaw portion 211 defining a tissue-treating surface 212. Proximal flange portion 216 of jaw member 210 is offset relative to the longitudinal axis of jaw member 210 (similarly as proximal flange portion 226 of jaw member 220) and is configured for positioning between pillar 223 of jaw member 220 and the distal end of shaft 202. Second pin 219 extends outwardly from proximal flange portion 216 of jaw member 210 towards drive bar 264 and is configured for receipt within the curved portion of the cam slot defined within drive bar 264. The offset configuration of proximal flange portion 216 of jaw member 210 allows drive bar 264 to extend alongside shaft 202 and proximal flange portions 216, 226 of jaw members 210, 220, respectively, such that first and second pins 209, 219, respectively, may be operably received within the cam slot of drive bar 264.

Distal jaw portion 211 of jaw member 210 further includes an alignment slot 213 defined therein that is offset relative to the longitudinal axis thereof. Alignment slot 213 extends in generally perpendicular orientation relative to tissue-treating surface 212 and is aligned within and configured to receive alignment pillar 223 of jaw member 220 to maintain the parallel orientation between jaw members 210, 220 regardless of the relative position of jaw members 210, 220. The use and operation of end effector assembly 200 is similar to that of end effector assembly 100 (FIG. 2) described above and, thus, will not be repeated here.

Figure 8:
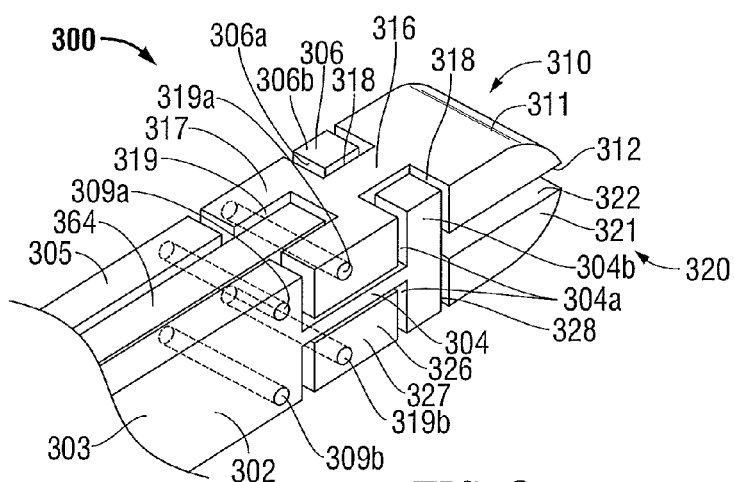
FIG. 8 is a perspective view of another end effector assembly configured for use with the forceps of FIG. 1.
Figure 9A:
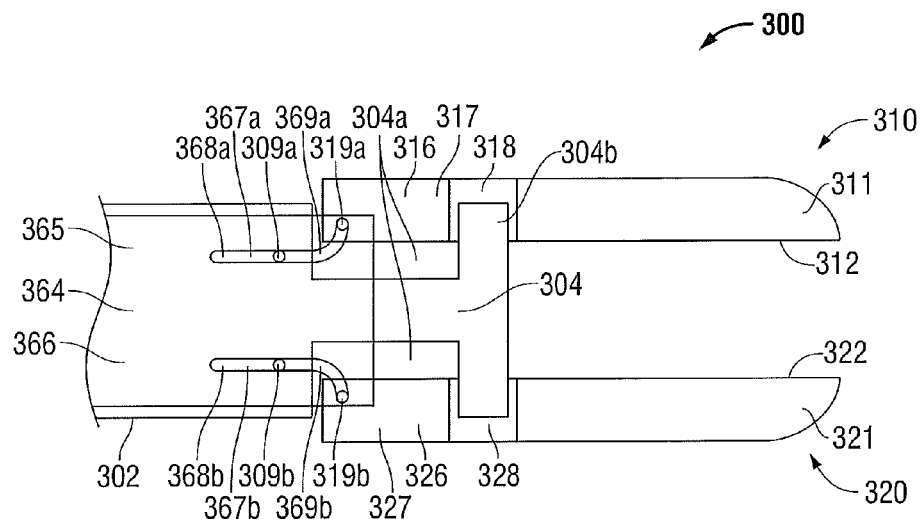
FIG. 9A is a longitudinal, cross-sectional view of the end effector assembly of FIG. 8 wherein the jaw members are disposed in the spaced-apart position.
Figure 9B:
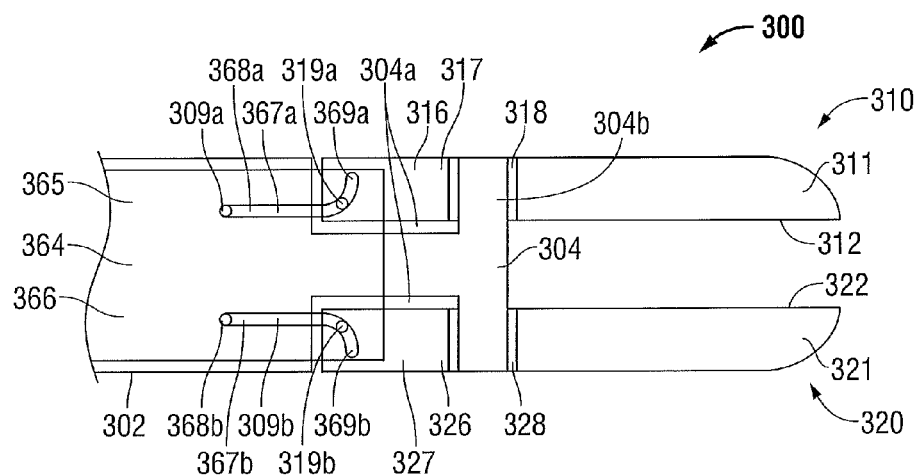
FIG. 9B is a longitudinal, cross-sectional view of the end effector assembly of FIG. 8 wherein the jaw members are disposed in the approximated position.
Figure 10A:
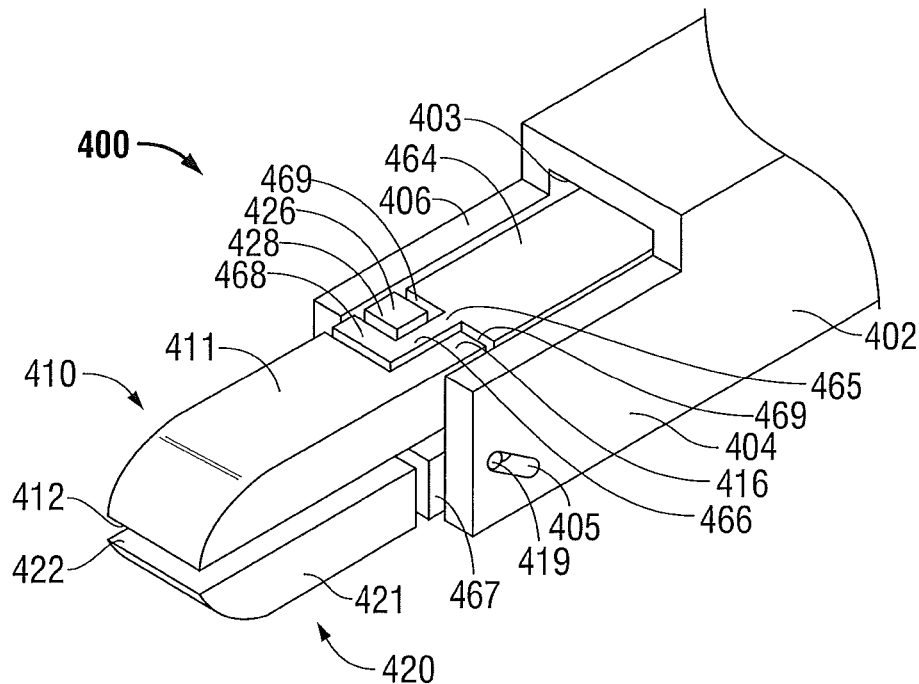
FIG. 10A is a side perspective view of another end effector assembly configured for use with the forceps of FIG. 1.
Figure 10B:
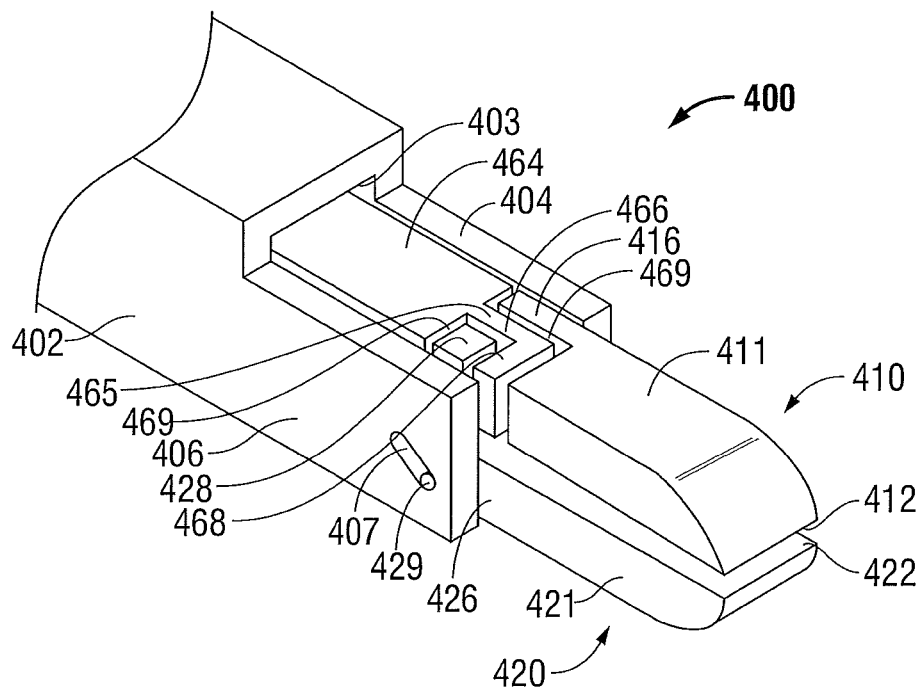
FIG. 10B is an opposite side perspective view of the end effector assembly of FIG. 10A.

Turning now to FIGS. 8 and 9A-9B, another embodiment of an end effector assembly similar to end effector assembly 100 (FIG. 2) and configured to achieve uniform and parallel jaw closure is shown generally identified by reference numeral 300. End effector assembly 300 differs from end effector assembly 100 (FIG. 2) mainly in that end effector assembly 300 defines a bilateral configuration, wherein both jaw members 310, 320 are movable relative to one another (in parallel fashion) and shaft 302 to move end effector assembly 300 between the spaced-apart and approximated positions, as opposed to the unilateral configuration of end effector assembly 100 (FIG. 2). For purposes of brevity, only the differences between end effector assembly 300 and end effector assembly 100 (FIG. 2) will be described in detail below, while similarities will only be summarily described or omitted entirely.

Continuing with reference to FIGS. 8 and 9A-9B, shaft 302 defines a bifurcated configuration having first and second spaced-apart shaft components 303, 305, respectively, and a longitudinal channel 307 extending therebetween. Longitudinal channel 307 is configured to slidably receive drive bar 364. Shaft 302 may alternatively be configured to define a longitudinally-extending lumen for receipt of drive bar 364 or may include upper and lower troughs that are configured to receive upper and lower portions of a bifurcated drive bar. The features and operation of end effector assembly 300 remain generally consistent regardless of the particular configuration provided. For the purposes herein, end effector assembly 300 is described hereinbelow with respect to shaft 302 having first and second spaced-apart shaft components 303, 305, respectively, and a longitudinal channel 307 extending therebetween.

With continued reference to FIGS. 8 and 9A-9B, each of the first and second shaft components 303, 305 includes a flange 304, 306, respectively, extending from the distal end thereof. Flanges 304, 306 each define generally T-shaped configurations having opposed, transverse cut-outs 304a, 306a, respectively, and a crossbar 304b, 306b, respectively. First and second shaft components 303, 305 further include upper and lower pins 309a, 309b, respectively, engaged thereto and extending therebetween. Upper and lower pins 309a, 309b are longitudinally aligned with one another but vertically offset relative to one another and extend transversely through longitudinal channel 307 of shaft 302 adjacent first and second flanges 304, 306 of shaft 302. Pins 309a, 309b, as will be described in greater detail below, are configured for engagement within respective upper and lower cam slots 367a, 367b defined within drive bar 364.

Drive bar 364, as mentioned above, is slidably received within longitudinal channel 307 defined between shaft components 303, 305. Drive bar 364 further includes upper and lower longitudinal portions 365, 366 that define mirror-image configurations of one another. More specifically, upper longitudinal portion 365 of drive bar 264 defines a transverse cam slot 367a therethrough towards the distal end thereof that includes a generally longitudinal portion 368a and a curved portion 369a that curves vertically upwardly from the longitudinal portion 368a. Lower longitudinal portion 366 of drive bar 364, on the other hand, defines a transverse cam slot 367b therethrough towards the distal end thereof that is a mirror-image of transverse cam slot 367a of upper longitudinal portion 365. That is, transverse cam slot 367b of lower longitudinal portion 366 includes a generally longitudinal portion 368b and a curved portion 369b that curves vertically downwardly from the longitudinal portion 368b. Upper and lower pins 309a, 309b of shaft 302 are configured for receipt with and longitudinal translation through longitudinal portions 368a, 368b of cam slots 367a, 367b, respectively.

With continued reference to FIGS. 8 and 9A-9B, Jaw members 310, 320 are movable relative to shaft 302 and one another from a spaced-apart position to an approximated position for grasping tissue therebetween (thus defining the bilateral configuration of end effector assembly 300). Each jaw member 310, 320 includes a proximal flange portion 316, 326, and a distal jaw portion 311, 321 that defines the respective tissue-treating surface 312, 322 thereof. As will be described in greater detail below, jaw members 310, 320 are configured such that tissue-treating surfaces 312, 322 remain disposed in parallel orientation relative to one another regardless of the relative positioning of jaw members 310, 320.

The proximal flange portion 316, 326 of each jaw member 310, 320 defines a T-shaped configuration that is offset 90 degrees relative to the T-shaped flanges 304, 306 of shaft components 303, 305, respectively. As a result of this configuration, proximal flange portions 316, 326 of jaw members 310, 320 and flanges 304, 306 of shaft 302 are configured for inter-fit engagement with one another to restrict movement of jaw members 310, 320 relative to one another to the vertical direction, thereby maintaining the parallel orientation of jaw members 310, 320 throughout movement of jaw members 310, 320 between the spaced-apart and approximated positions. More specifically, to inter-fit jaw members 310, 320 and shaft 302 to one another, the first and second ends of crossbars 317, 327 of T-shaped proximal flange portions 316, 326 of jaw members 310, 320, respectively, are received within transverse cut-outs 304a, 304b of respective flanges 304, 306 of shaft 302. Further, the first and second ends of crossbars 304b, 306b of T-shaped flanges 304, 306 of shaft 302 are received within transverse cut-outs 318, 328 of proximal flange portions 316, 326 of jaw members 310, 320, respectively. Similarly as described above with respect to pillars 123 and alignment slots 113 of jaw members 120, 110, respectively (see FIGS. 2 and 4-6), one or more of the cut-outs 304a, 306a, 318, 328 and/or crossbars 304b, 306b, 317, 327 may include "keying" features to further ensure parallel movement and orientation of jaw members 310, 320 relative to one another.

Continuing with reference to FIGS. 8 and 9A-9B, crossbars 317, 327 of proximal flange portions 316, 326 of jaw members 310, 320, respectively, each define a central recess 319 (the central recesses of crossbars 317, 327 are similar to one another and are collectively designated by reference numeral 319; however, only recess 319 of proximal flange portion 316 is shown). A second pair of pins including upper and lower pins 319a, 319b, respectively, that are longitudinally aligned but vertically offset relative to one another, are fixedly engaged within and extend transversely through the central recesses 319 of proximal flange portions 316, 326 of jaw members 310, 320, respectively. Pins 319a, 319b are configured for engagement within respective cam slots 367a, 367b of upper and lower longitudinal portions 365, 366 of drive bar 364. More specifically, upper and lower pins 319a, 319b are configured for receipt with and translation through curved portions 369a, 369b of cam slots 367a, 367b, respectively.

The use and operation of end effector assembly 300 for moving jaw members 310, 320 from the spaced-apart position to the approximated position to grasp tissue therebetween is described with reference to FIGS. 8-9B. The full use and operation of end effector assembly 300 is similar to that described above with respect to end effector assembly 100 (FIG. 2) and, thus, similarities will only be summarily described or omitted entirely.

Initially, jaw members 310, 320 are disposed in the spaced-apart position (FIG. 9A). In this position, first pins 309a, 309b are disposed at the distal ends of longitudinal portions 368a, 368b of cam slots 367a, 367b, respectively, while second pins 319a, 319b are disposed at the first ends (e.g., vertically-spaced from longitudinal portions 368a, 368b and one another) of curved portions 369a, 369b of cam slots 367a, 367b, respectively. As such, with second pins 319a, 319b of jaw members 310, 320, respectively, vertically-spaced from one another, jaw members 310, 320 are likewise vertically-spaced from one another, e.g., in the spaced-apart position. Further, in the spaced-apart position, the ends of crossbars 304b, 306b, 317, 327 are only partially disposed within cut-outs 318, 328, 304a, 306a but sufficiently so as to maintain the parallel orientation of tissue-treating surfaces 312, 322 of jaw members 310, 320, respectively.

In order to grasp tissue between tissue-treating surfaces 312, 322 of jaw members 310, 320, respectively, movable handle 40 (FIG. 1) is compressed, or pulled proximally relative to fixed handle 50 (FIG. 1) from the initial position to the compressed position to urge drive bar 364 distally. As drive bar 364 is translated distally through longitudinal channel 307 of shaft 302 relative to end effector assembly 300, first pins 309a, 309b are moved through longitudinal portions 368a, 368b of cam slots 367a, 367b from the distal ends thereof towards the proximal ends thereof. At the same time, second pins 319a, 319b are moved vertically through curved portions 369a, 369b of cam slots 367a, 367b towards one another. That is, as drive bar 364 is advanced distally, upper second pin 319a of jaw member 310 is translated vertically downwardly through curved portion 369a of cam slot 367a to move jaw member 310 downwardly relative to shaft 302 and jaw member 320, while lower second pin 319b of jaw member 320 is translated vertically upwardly through curved portion 369b of cam slot 367b to move jaw member 320 upwardly relative to shaft 302 and jaw member 310 until jaw members 310, 320 achieve the approximated position grasping tissue therebetween. The inter-fitting between crossbars 304b, 306b, 317, 327 and cut-outs 318, 328, 304a, 306a, as mentioned above, maintains jaw members 310, 320 in parallel orientation relative to one another by restricting movement of jaw members 310, 320 relative to one another to the vertical direction.

Turning now to FIGS. 10A-12B, another embodiment of an end effector assembly provided in accordance with the present disclosure and configured for use with forceps 10 (FIG. 1) is shown generally identified by reference numeral 400. End effector assembly 400 is similar to end effector assembly 300 (FIGS. 8-9B) and, thus, only the differences between end effector assembly 400 and end effector assembly 300 (FIGS. 8-9B) will be described in detail below, while similarities will be summarily described or omitted entirely.

Continuing with reference to FIGS. 10A-12B, shaft 402 defines a longitudinally-extending lumen 403 therethrough for slidably receiving drive bar 464. Shaft 402 further includes a bifurcated distal end including first and second spaced-apart flanges 404, 406, respectively. Each flange 404, 406 defines an angled transverse cam slot 405, 407, respectively, therethrough towards the free end thereof. Cam slots 405, 407 are sloped similarly relative to one another but are positioned and angled oppositely, e.g., cam slot 405 is disposed towards a lower side of flange 404 and angles upwardly in the distal to proximal direction, while cam slot 407 is disposed towards an upper side of flange 406 and angles downwardly in the distal to proximal direction (although this configuration may be reversed). As will be described below, cam slots 405, 407 are configured to respectively receive first and second pins 419, 429 of jaw members 410 420, respectively.

Figure 11B:
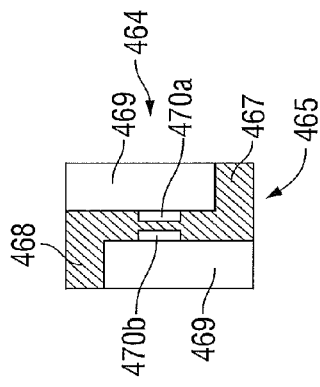
FIG. 11B is a transverse, cross-sectional view taken along section line 11B-11B of FIG. 11A.

With reference to FIGS. 10A-11B in particular, drive bar 464, as mentioned above, is slidably received within lumen 403 of shaft 402. Drive bar 464 includes a distal engagement portion 465 having a neck 466 and first and second laterally-extending flanges 467, 468, respectively, disposed at the free end of neck 466. The reduced width of neck 466 relative to drive bar 464 and flanges 467, 468 forms a pair of cut-outs 469 between flanges 467, 468 and the distal end of drive bar 464. Neck 466 further includes a vertically-elongated recess 470a, 470b defined therein on each lateral side thereof. Recesses 470a, 470b are configured to respectively slidably receive pins 419, 429 of jaw members 410, 420. Further, as best shown in FIG. 11B, first flange 467 extends laterally from a lower portion of neck 466 in a first direction, while second flange 468 extends laterally from an upper portion of neck 466 in a second, opposite direction.

Referring again to FIGS. 10A-12B, jaw members 410, 420 are each movable relative to shaft 402 and one another from a spaced-apart position to an approximated position for grasping tissue therebetween. Jaw members 410, 420 are similar to one another with each defining a proximal flange portion 416, 426 and a distal jaw portion 411, 421 that defines the respective tissue-treating surface 412, 422 thereof. End effector assembly 400 is configured such that tissue-treating surfaces 412, 422 of jaw members 410, 420, respectively, remain disposed in parallel orientation relative to one another regardless of the relative positioning of jaw members 410, 420.

Figure 12B:
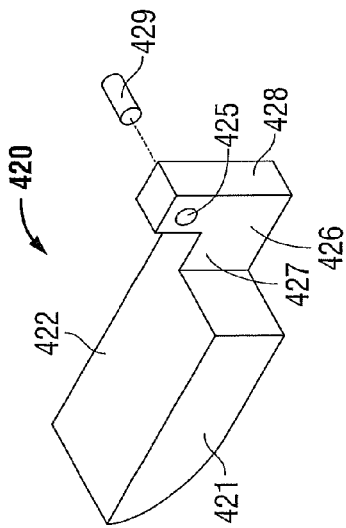
FIG. 12B is a side perspective view of the other jaw member of the end effector assembly of FIG. 11A.
Figure 11A:
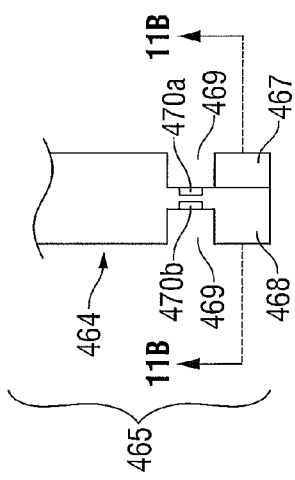
FIG. 11A is a top view of a distal end of a drive bar configured for use with the end effector assembly of FIG. 10A.
Figure 12A:
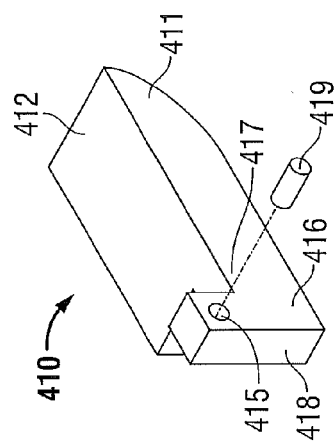
FIG. 12A is a side perspective view of a jaw member of the end effector assembly of FIG. 11A.

As best shown in FIGS. 12A-12B, proximal flange portions 416, 426 of jaw members 410, 420 each define a proximally-extending portion 417, 427 and an upright portion 418, 428 that defines an aperture 415, 425 configured to receive the respective pin 419, 429 therethrough. Proximal flange portions 416, 426 are offset on opposite sides of a longitudinal axis of end effector assembly 400 and are configured for inter-fit engagement with distal portion 465 of drive bar 464 (see FIGS. 11A-11B). More specifically, with additional reference to FIGS. 10A-11B, upright portions 418, 428 of proximal flanges 416, 426 are configured for receipt within cut-outs 469 defined within distal engagement portion 465 of drive bar 464 such that vertically-elongated recesses 470a, 470b are longitudinally aligned with apertures 415, 425, respectively, while flanges 467, 468 of distal engagement portion 465 of drive bar 464 are disposed adjacent proximally-extending portions 417, 427 of jaw members 410, 420 between the upright portions 418, 428 of the respective jaw member 410, 420 and the distal jaw portion 421, 411 of the other jaw member 420, 410. This inter-fit engagement between drive bar 464 and jaw members 410, 420 maintains the parallel orientation of jaw members 410, 420 relative to one another by restricting movement of jaw members 410, 420 relative to one another to the vertical direction, similarly as described above. Further, as also described above, proximal flange portions 416, 426 of jaw members 410, 420, respectively, and/or distal engagement portion 465 of drive bar 464 may include additional features to establish a "keyed" relationship therebetween.

First and second pins 419, 429 of jaw members 410, 420, respectively, are configured for engagement within respective cam slots 405, 407 of flanges 404, 406 of shaft 402, respective apertures 415, 425 of jaw members 410, 410, and respective vertically-elongated recesses 470a, 470b of neck 466 of drive bar 464. As a result of this configuration, longitudinal translation of drive bar 464 urges pins 419, 429 to translate along cam slots 405, 407 which, in turn, urge pins 419, 429 to translate vertically within vertically-elongated recesses 470a, 470b of neck 466 of drive bar 464 such that jaw members 410, 420 are moved relative to one another between the spaced-apart position and the approximated position while maintaining the parallel orientation between tissue-treating surfaces 412, 422 of jaw members 410, 420, respectively. More specifically, the inter-fit engagement between proximal flange portions 416, 426 of jaw members 410, 420, respectively, and distal engagement portion 465 of drive bar 464 maintains the parallel orientation of jaw members 410, 420 relative to one another by restricting movement of jaw members 410, 420 relative to one another to the vertical direction. The use and operation of end effector assembly 400 is similar to that described above with respect to the previous embodiments and, thus, will not be repeated here to avoid unnecessary repetition.

Figure 13:
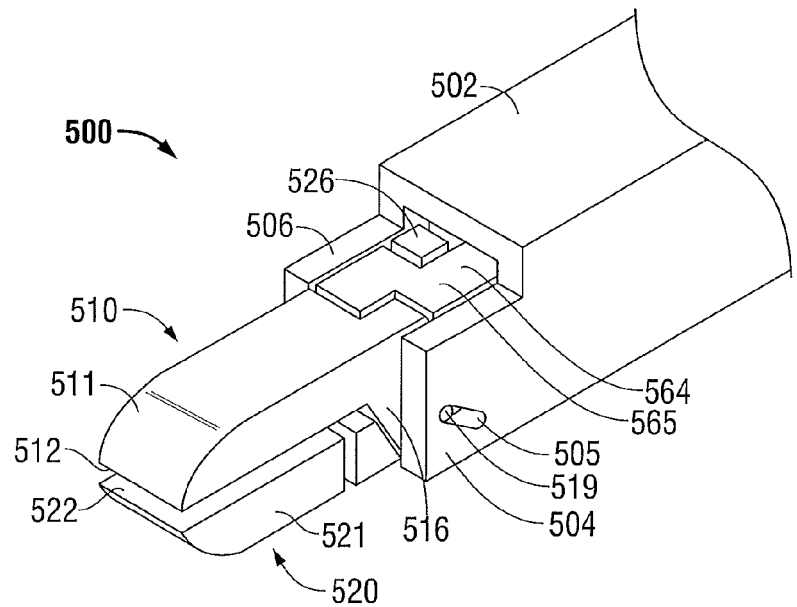
FIG. 13 is a side perspective view of another end effector assembly configured for use with the forceps of FIG. 1.
Figure 14A:
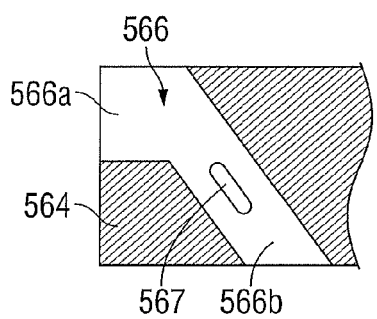
FIG. 14A is a longitudinal cross-sectional view of a first side of a distal end of a drive bar configured for use with the end effector assembly of FIG. 13.
Figure 14B:
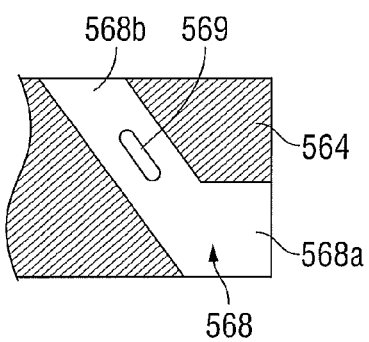
FIG. 14B is a longitudinal cross-sectional view of a second, opposite side of the distal end of the drive bar of FIG. 14A.
Figure 15:
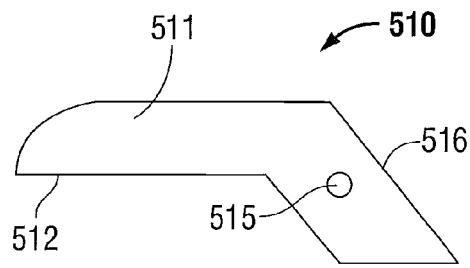
FIG. 15 is a side view of a jaw member of the end effector assembly of FIG. 13.

With reference to FIGS. 13-15, another embodiment of an end effector assembly provided in accordance with the present disclosure and configured for use with forceps 10 (FIG. 1) is shown generally identified by reference numeral 500. End effector assembly 500 is similar to end effector assembly 400 (FIGS. 10A-12B) and, thus, only the differences therebetween will be described in detail hereinbelow for purposes of brevity. In particular, end effector assembly 500 differs from end effector assembly 400 (FIGS. 10A-12B) mainly in that the components of end effector assembly 500 define angled configurations, rather than vertical configurations such that, while jaw members 510, 520 remain disposed in parallel orientation relative to one another throughout movement of jaw members 510, 520 between the spaced-apart and approximated positions, jaw members 510, 520 are also moved longitudinally relative to shaft 502 as jaw members jaw members 510, 520 are moved between the spaced-apart and approximated positions.

Continuing with reference to FIGS. 13-15, shaft 502 is configured to slidably receive drive bar 564 and includes a bifurcated distal end having first and second spaced-apart flanges 504, 506 extending distally therefrom. Flanges 504, 506 each define an angled transverse cam slot 505 (only the cam slot 505 of flange 504 is shown). The cam slots 505 are sloped similarly relative to one another but are positioned and angled oppositely, similarly as described above with respect to shaft 402 and end effector assembly 400 (FIGS. 10A-12B). Cam slots 505 are configured to receive first and second pins 519 of jaw members 510, 520 (only pin 519 of jaw member 510 is shown).

Drive bar 564, as mentioned above, is slidably received within shaft 502. Drive bar 564 includes a distal engagement portion 565 defining first and second cut-outs 566, 568 (FIGS. 14A, 14B, respectively) on opposite sides of drive bar 564. Each cut-out 566, 568 includes a longitudinal portion 566a, 568a and an angled portion 566b, 568b, respectively. Longitudinal portion 566a of cut-out 566 extends along an upper portion of drive bar 564, while longitudinal portion 568a of cut-out 568 extends along a lower portion of drive bar 564. Angled portions 566b, 568b are angled similar in slope but opposite in direction relative to one another. Further, an angled elongated recess 567, 569 is defined within drive bar 564 adjacent angled portions 566b, 568b of respective cut-outs 566, 568. Recesses 567, 569 are angled similarly to their respective cut-outs 566, 568 and, thus, oppositely relative to one another. Recesses 567, 569 are configured to respectively receive the first and second pins 519 of jaw members 510, 520.

Referring still to FIGS. 13-15, jaw members 510, 520 are each movable relative to shaft 502 in a diagonal direction including both vertical and longitudinal directional components and relative to one another in a vertical direction only between a spaced-apart position and an approximated position for grasping tissue therebetween. End effector assembly 500 is configured such that tissue-treating surfaces 512, 522 of jaw members 510, 520, respectively, remain disposed in parallel orientation relative to one another regardless of the relative positioning of jaw members 510, 520. Jaw member 510 includes a proximal flange portion 516 and a distal jaw portion 511 that defines the tissue-treating surface 512 of jaw member 510. Jaw member 520 likewise includes a proximal flange portion 526 and a distal jaw portion 521 that defines the tissue-treating surface 522 of jaw member 520. In fact, jaw members 510, 520 are similar to one another and, thus, only jaw member 510 will be described hereinbelow, keeping in mind that jaw member 520 includes similar features and functions similarly.

Jaw member 510, as mentioned above, includes a distal jaw portion 511 and a proximal flange portion 516. Proximal flange portion 516 defines an angled configuration that slopes similarly to angled portion 566b of cut-out 566 defined within drive bar 564. Proximal flange portion 516 further defines an aperture 515 therethrough that is configured to receive pin 519. That is, pin 519 is configured for engagement within cam slot 505 of flange 504 of shaft 502, aperture 515 of proximal flange portion 516 of jaw member 510, and angled recess 567 of drive bar 564. The pin (not explicitly shown) of jaw member 520 is similarly configured for engagement within the cam slot (not explicitly shown) of flange 506 of shaft 502, the aperture (not explicitly shown) defined within the proximal flange portion 526 of jaw member 520, and angled recess 569 of drive bar 564. Further, proximal flange portions 516, 526 of jaw members 510, 520, respectively, are configured for inter-fit engagement with drive bar 564 similarly as described above with respect to the previous embodiments, except that, due to the angled configuration of angled portions 566b, 568b of cut-outs 566, 568 and angled proximal flange portions 516, 526 of jaw members 510, 520, respectively, movement of jaw members 510, 520 is restricted to diagonal movement along the similarly-sloped angled portions 566b, 568b of cut-outs 566, 568 defined within drive bar 564. However, since angled portions 566b, 568b of cut-outs 566, 568 are similarly-sloped relative to one another (in opposite directions), tissue-treating surfaces 512, 522 of jaw members 510, 520, respectively, are maintained in parallel orientation relative to one another regardless of the position of jaw members 510, 520 relative to one another, e.g., the spaced-apart position, the approximated position, or any position therebetween.

With continued reference to FIGS. 13-15, in use, longitudinal translation of drive bar 564 urges pin 519 of jaw member 510 to translate along cam slot 505 of flange 504 of shaft 502 which, in turn, urges pin 519 to translate along angled recess 567 of drive bar 564 such that proximal flange portion 516 of jaw member 510 is moved along angled portion 566b of cut-out 566 of drive bar 564. At the same time, the longitudinal translation of drive bar 564 urges the pin (not explicitly shown) of jaw member 520 to translate along the cam slot (not explicitly shown) of flange 506 of shaft 502 which, in turn, urges the pin (not explicitly shown) to translate along angled recess 569 of drive bar 564 such that proximal flange portion 526 of jaw member 520 is moved along angled portion 568b of cut-out 568 of drive bar 564 in an opposite vertical direction but similar longitudinal direction as jaw member 520. More specifically, distal translation of drive bar 564 effects movement of jaw members 510, 520 vertically towards one another, e.g., towards the approximated position, while simultaneously advancing jaw members 510, 520 in concert distally relative to shaft 502. Proximal translation of drive bar 564, on the other hand, effects movement of jaw members 510, 520 vertically apart from one another, e.g., towards the spaced-apart position, while simultaneously retracting jaw members 510, 520 in concert proximally relative to shaft 502. As mentioned above, due to the configuration of shaft 502, drive bar 564, and jaw members 510, 520, and due to the inter-fit engagement between proximal flange portions 516, 526 of jaw members 510, 520, respectively, and drive bar 564, tissue-treating surfaces 512, 522 of jaw members 510, 520, respectively, are maintained in parallel orientation relative to one another. The use and operation of end effector assembly 500 is otherwise similar to that described above with respect to the previous embodiments.

Turning to FIGS. 1, 3, and 16-17B, as mentioned above, forceps 10 may incorporate a knife assembly 180 for cutting tissue grasped between jaw members 110, 120. Knife assembly 180 may be provided for use with any of the end effector assemblies provided herein, or any other suitable end effector assembly. For the purposes herein, knife assembly 180 is described with reference to forceps 10 and end effector assembly 100.

Knife assembly 180 includes a knife bar 182 that is coupled to trigger assembly 80 via ferrule 89 at the proximal end thereof and to knife 184 at the distal end thereof. Knife bar 182 defines a transverse cam slot 187 therethrough towards distal end 186 thereof. Cam slot 187 defines a generally longitudinal portion 188 having proximal and distal ends 188a, 188b, respectively, and a curved portion 189 that curves vertically upwardly from the longitudinal portion 188. Curved portion 189 includes a first (lower, proximal) end 189a and second (upper, distal) end 189b. Cam slot 187 is configured to first and second pins 190, 192 within respect longitudinal and curved portions 188, 189, respectively, thereof.

With continued reference to FIGS. 1, 3, and 6-17B, knife 184, as mentioned above, is disposed within knife channel 125 defined within jaw member 120 (although knife 184 may alternatively be disposed within knife channel 115 of jaw member 110) and is configured, upon actuation of trigger 82 of trigger assembly 80, to move from the retracted position, wherein knife 184 is disposed completely within knife channel 125 of jaw member 120, to the extended position, wherein knife 184 extends from knife channel 125, between jaw members 110, 120, and at least partially into knife channel 115 of jaw member 110, to cut tissue grasped between jaw members 110, 120.

First pin 190 is fixedly engaged within jaw member 120 and extends transversely through knife channel 125 of jaw member 120. Although first pin 190 is shown disposed at a proximal end of knife 184, first pin 190 may alternatively be centrally disposed, or may be disposed at a distal end of knife 184. As mentioned above, first pin 190 is configured to be slidably disposed within longitudinal portion 188 of cam slot 187. Second pin 192 is fixedly engaged to and is disposed transversely relative to knife 184. As mentioned above, second pin 192 is configured to be slidably disposed within curved portion 189 of calm slot 187. This configuration, wherein first pin 190 of jaw member 120 is slidably disposed within longitudinal portion 188 of cam slot 187 and second pin 192 of knife 184 is slidably disposed within curved portion 189 of cam slot 187, allows knife 184 to be vertically translated relative to jaw members 110, 120 between the retracted and extended positions to cut tissue grasped therebetween upon longitudinal translation of knife bar 182, as will be described in greater detail below.

The use and operation of knife assembly 180 in conjunction with forceps 10 and end effector assembly 100 for cutting tissue grasped between jaw members 110, 120 is described with reference to FIGS. 1, 3 and 16-17B. After tissue treatment (or after moving jaw members 110, 120 to the approximated position to grasp tissue therebetween in procedures where tissue treatment is not required) jaw members 110, 120 are disposed in the approximated position and knife 184 is disposed in the retracted position (FIG. 17A). At this point, trigger 82 is disposed in the un-actuated position and, accordingly, knife bar 182 is disposed in a more-distal position such that knife 184 is disposed in the retracted position. More specifically, in the retracted position, as best shown in FIG. 17A, first pin 190 is disposed at proximal end 188a of longitudinal portion 188 of cam slot 187 of knife bar 182, while second pin 192 is disposed at first (lower, proximal) end 189a of curved portion 189 of cam slot 187. In this position, wherein first and second pins 190, 192 are longitudinally-aligned with one another, knife 184 is disposed within knife channel 125 in the retracted position.

In order to move knife 184 to the extended position to cut tissue grasped between tissue-treating surfaces 112, 122 of jaw members 110, 120, respectively, trigger 82 of trigger assembly 80 is actuated from the un-actuated position to the actuated position to urge knife bar 182 proximally relative to end effector assembly 100. As knife bar 184 is translated proximally, first pin 190 is moved through longitudinal portion 188 of cam slot 187 from the proximal end 188a thereof towards the distal end 188b thereof, while second pin 192 is moved through curved portion 189 of cam slot 187 from the first (lower, proximal) end 189a thereof towards the second (upper, distal) end 189b thereof. As second pin 192 is urged vertically upwardly due to the vertically-curved configuration of curved portion 189 of cam slot 187 and the proximal translation of knife bar 182 relative to second pin 192, knife 184 is moved vertically upwardly to extend from jaw member 120 to the extended position to cut tissue grasped between jaw members 110, 120. That is, in the extended position, as best shown in FIG. 17B, first pin 190 is disposed at distal end 188b of longitudinal portion 188 of cam slot 187, while second pin 192 is disposed at second (upper, distal) end 189b of curved portion 189 of cam slot 187.

Once tissue has been cut, knife 184 may be returned to the retracted position and jaw members 110, 120 may be returned to the spaced-apart position to release the treated and/or divided tissue. More specifically, in order to return knife 184 to the retracted position, trigger 82 is released (or returned) to the un-actuated position, thereby translating knife bar 182 distally to return knife 184 to the retracted position.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
an end effector assembly including first and second jaw members disposed in parallel orientation relative to one another, at least one of the jaw members movable along a first axis relative to the other jaw member between a spaced-apart position and an approximated position for grasping tissue therebetween, the first and second jaw members configured to maintain the parallel orientation therebetween upon movement of the jaw members between the spaced-apart and approximated positions; and
a drive bar coupled to the at least one jaw member, the drive bar selectively movable along a second axis that is different from the first axis between first and second positions for moving the jaw members between the spaced-apart and approximated positions, wherein the first and second jaw members are coupled to an outer shaft and wherein the drive bar is selectively movable along the second axis relative to the outer shaft, and wherein the drive bar defines at least one cam slot, a first portion of the cam slot defining a longitudinal configuration and a second portion of the cam slot extending in a generally diagonal direction relative to the first portion, the first portion of the cam slot configured to slidably receive a pin of the outer shaft and the second portion of the cam slot configured to slidably receive a pin of at least one of the jaw members such that translation of the drive bar along the second axis effects movement of the at least one jaw member along the first axis.

2. The forceps according to claim 1, wherein the first and second axes are perpendicular to one another.

3. The forceps according to claim 1, wherein the at least one of the jaw members is configured for slidable inter-fit engagement with the outer shaft to restrict movement of the jaw members to along the first axis, thereby maintaining the parallel orientation between the jaw members upon movement of the jaw members between the spaced-apart and approximated positions.

4. The forceps according to claim 3, wherein the outer shaft and the at least one jaw member each include a T-shaped flange, the T-shaped flanges configured for slidable inter-fit engagement with one another.

5. The forceps according to claim 1, wherein the first and second jaw members are configured for slidable inter-fit engagement with one another to restrict movement of the jaw members to along the first axis, thereby maintaining the parallel orientation between the jaw members upon movement of the jaw members between the spaced-apart and approximated positions.

6. The forceps according to claim 5, wherein at least one of the jaw members includes an alignment pillar and wherein at least one of the jaw members includes an alignment slot, the alignment pillars and alignment slots slidably inter-fit with one another to inhibit relative movement of the jaw members off of the first axis.

7. The forceps according to claim 1, wherein at least of the one jaw members is configured for slidable inter-fit engagement with the drive bar to restrict movement of the at least one jaw member to along the first axis, thereby maintaining the parallel orientation between the jaw members upon movement of the jaw members between the spaced-apart and approximated positions.

8. The forceps according to claim 7, wherein the first and second jaw members are slidable diagonally along the first axis and wherein the drive bar is selectively translatable longitudinally along the second axis.

* * * * *